United States Patent [19]

Payne et al.

[11] Patent Number: 4,863,433
[45] Date of Patent: Sep. 5, 1989

[54] SYRINGE

[75] Inventors: John B. Payne, West Des Moines, Iowa; Davis R. Jones, West Palm Beach, Fla.

[73] Assignee: Diamond Scientific Co., Des Moines, Iowa

[21] Appl. No.: 197,636

[22] Filed: May 23, 1988

[51] Int. Cl.⁴ .............................................. A61M 5/32
[52] U.S. Cl. ..................................................... 604/194
[58] Field of Search ................ 604/194, 193, 195, 187

[56] References Cited

U.S. PATENT DOCUMENTS 3,107,785 10/1963 Roehr ................................... 604/194
4,390,016 6/1983 Riess .................................... 604/194

FOREIGN PATENT DOCUMENTS 0025408 2/1907 United Kingdom ................ 604/194

Primary Examiner—John D. Yasko

[57] ABSTRACT

A syringe is provided which has a barrel, a plunger having a hollow center, with the needle stored in the hollow center. A storage compartment is used to encase the needle and keep it sterile while being stored within the plunger. A cap on the tip of the barrel having a protruding shoulder securely engages the tip of the barrel while being stored, and assists in preventing leakage of inoculant from the barrel of the syringe.

4 Claims, 2 Drawing Sheets

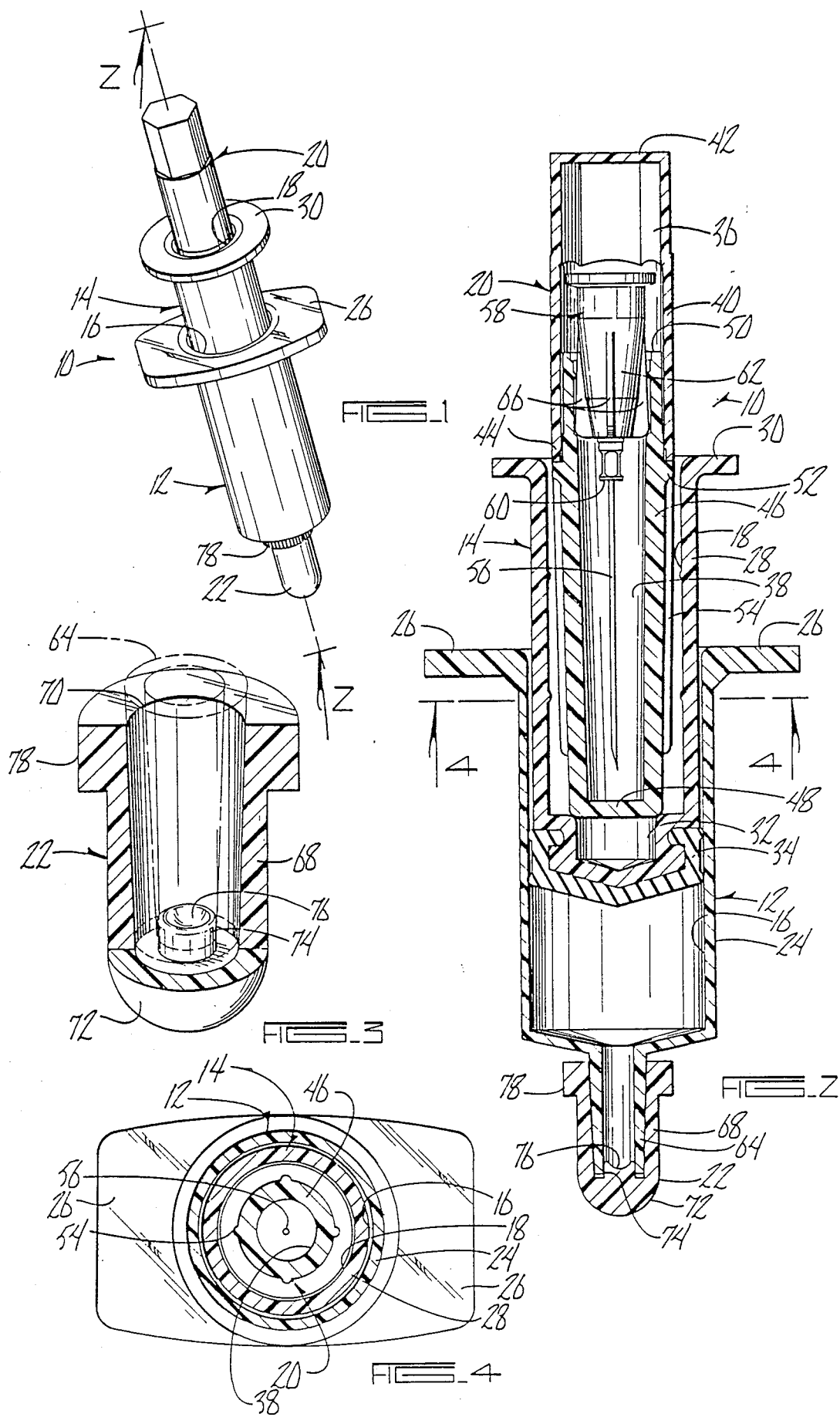

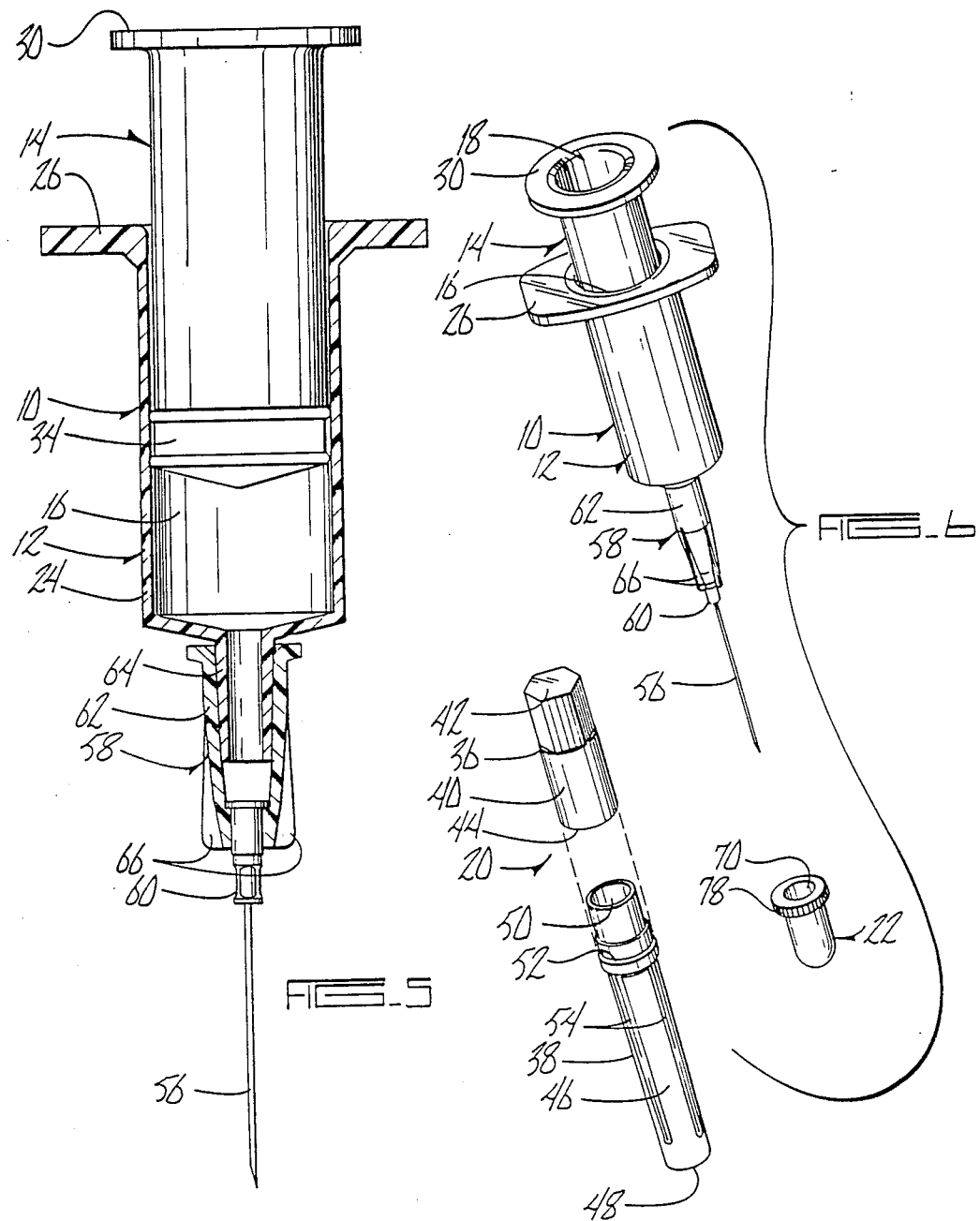

SYRINGE

BACKGROUND OF THE INVENTION

Syringes consist of a barrel, a plunger, a tip in the barrel and a hollow needle which is attached to the tip of the barrel. Putting together these basic components of the syringe can be somewhat cumbersome and time consuming, especially since many of these different parts are packaged separately. If the needle is packaged separately, it must be removed from a separate box or compartment, and then placed upon the tip of the barrel. Then the needle is ordinarily inserted into a bottle which contains the fluid to be injected, and the fluid withdrawn from the bottle using the plunger as suction until it can be seen that the appropriate amount has been withdrawn into the syringe. This observation is usually made by readings upon the side of the barrel. If the syringe is packaged with the needle already attached to the barrel, the liquid still must be measured from the bottle into the syringe, and additional problems exist with storage and the problem of breakage. These current methods of transporting syringes are especially cumbersome to veterinarians, for example, who, when treating large animals, must travel from one client operation to another while carrying all of the necessary equipment for inoculation. This may necessitate separate boxes for needles, barrels and plungers, and liquid, taking up a considerable amount of space. Further, when working in the field, it can be time consuming and difficult to locate the needle, attach it to the barrel, and withdraw the appropriate amount of inoculant while reading the measurements along the side of the barrel.

This invention provides a means of storing all the separate components of a syringe within itself, eliminating the necessity of separate packaging, and providing for a small and compact storage means. Further, the inoculant may be provided already within the syringe, eliminating the need to measure the inoculant from a separate bottle.

SUMMARY OF THE INVENTION

This invention relates to a syringe which includes a hollow plunger within which the needle of the syringe may be stored. A storage container surrounding the needle keeps it sterile and prevents damage or injury. The inoculant may be stored within the barrel of the syringe, and is prevented from leaking by a cap on the tip of the barrel which removably seals the inoculant in place.

Accordingly, it is an object of this invention to provide for a syringe which acts as its own container for the various component parts.

Another object is to provide a syringe in which the component parts occupy only a small area of space.

A further object of the invention is to provide for a syringe in which the inoculant may be contained within the barrel of the syringe.

Yet another object is to provide a syringe which eliminates the need to visually measure the amount of inoculant required for vaccination.

Another object is to provide a safe and sterile means of transporting syringe and inoculant.

Yet another object is to prevent leakage of inoculant from the barrel of the syringe during storage.

A still further object is to decrease the amount of time necessary to put a syringe together for use.

BRIEF DESCRIPTION OF THE DRAWINGS

FIG. 1 is a side plan view showing the syringe of the invention when stored.

FIG. 2 is a cross-sectional view of the syringe of the invention taken along lines 2—2 of FIG. 1.

FIG. 3 is a perspective cross-sectional view of the cap of the invention.

FIG. 4 is a cross-sectional view taken along lines 4—4 of FIG. 2.

FIG. 5 is a side cross-sectional view showing the syringe ready to use.

FIG. 6 is an exploded perspective view showing the needle removed and attached to the syringe.

DETAILED DESCRIPTION OF THE INVENTION

The syringe of the invention is represented at 10, and as can be seen in FIG. 1, all the component parts may be stored within the syringe itself. It includes a barrel 12 having a plunger 14 slidably inserted within the hollow center of the barrel 16. The invention provides also for a hollow center of the plunger 18, within which is placed a storage compartment 20 which encases the hollow needle (not pictured in FIG. 1) of the syringe. Cap 22 is attached to the other end of barrel 12 and retains any inoculant fluid within the barrel 12.

FIG. 2 shows details of these component parts. Barrel 12 consists of cylindrical side walls 24 with flanges 26 at one end of the barrel 12. These flanges 26 are used during inoculation by grasping with the fingers in order to steady the barrel 12. Plunger 14 also consists of cylindrical side walls 28 and flanges 30. The flanges 30 of plunger 14 are used during inoculation to provide downward pressure on plunger 14 so that plunger 14 may be moved towards barrel 12, and the inoculant within the barrel 12 forced out. Plunger 14 also contains at the end opposite flanges 30, a plastic stopper 32 inserted within a larger rubber stopper 34 which abuts the cylindrical walls 24 of barrel 12. The stopper 34 forces inoculant out through the barrel 12. These stoppers are standard components of a typical syringe.

As noted, plunger 14 includes a hollow center 18 within which is placed storage compartment 20. Storage compartment 20 includes upper portion 36 and lower portion 38. Upper portion 36 has cylindrical walls 40 and a closed end 42, and opposite open end 44. Similarly, lower portion 38 has cylindrical walls 46, closed end 48, and opposite open end 50. Lower portion open end 50, in this embodiment, is of a narrower circumference than open end 44 of upper portion 36. It is also provided with shoulder 52. In this manner, lower portion 38 at its open end 50 may be slipped within open end 44 of upper portion 36. Shoulder 52 prevents further movement of open end 44 of upper portion 36. Thus, lower portion 38 may be snapped into upper portion 36 providing for a removable secure engagement. Storage compartment 20 may also be provided with fins 54 which prevent wobbly movement of storage container 20 while within a hollow center 18 of plunger 14.

Storage compartment 20 contains with it hollow needle 56 of syringe 10. Hollow needle 56 has attached to it a holding means 58. This may take any number of forms, and here is shown as including a lower conical member 60 within which hollow needle 56 is encased. This lower conical member 60 is partially fit within an upper conical member 62. This upper conical member, is of a size and shape adapted to be fit over the tip 64 of barrel 12 when the syringe is to be used. This embodiment also includes fins 66 on upper conical portion 62 of the holding means 58. The fins 66 allow for engagement of holding means 58 to lower portion 38 of storage compartment 20. In this manner, lower portion 38 of the storage compartment 20 engages the fins 66, while allowing hollow needle 56 to be secured without touching the cylindrical side walls 46 of lower portion 38. This aids in keeping the hollow needle 56 sanitary.

At the opposite end of barrel 12, tip 64 is fit with a cap 22. Details of cap 22 are shown in FIG. 3. Cap 22 includes cylindrical side walls 68, open end 70, and an opposite closed end 72. A cylindrical shoulder 74 may be provided which protrudes from closed ends 72 interior to the cap 22. This embodiment provides for a concave center 76 of the shoulder 74. In this manner, when the cap 22 is slipped over tip 64 protruding shoulder 74 provides a secure engagement with tip 64. Concave center 76 further aids in sealing tip 64, and preventing any leakage of inoculant from barrel 12. With this type of construction, it has been found that the cap 22 provides a very strong sealing of the inoculant within the barrel 12. This prevents inoculant from being removed should the plunger 14 be accidentally activated. While cap 22 provides strong sealing engagement with tip 64, it is also easily removed by hand. A corrugated portion 78 may be provided at the outer edge of open ends 70 of cap 22 allowing for easy gripping during removal.

FIG. 5 shows the syringe assembled from its stored position, and ready to use.

As shown from the above, and also demonstrated in FIG. 6, needle 22 is stored within the storage compartment 20 and placed within the hollow center 18 of plunger 14. Cap 22 firmly seals the tip 64 of barrel 12, retaining the inoculant within the barrel during storage. When the syringe is ready to be used, cap 22 is removed by gripping corrugated portion 78 and pulling it from the tip 64. Storage compartment 20 is removed from hollow center 18 of plunger 14, and upper portion 36 removed from lower portion 38 of storage compartment 20. Lower portion 38 remains engaged with fins 66 of holding means 58 for the hollow needle 56, while the upper conical member 62 of holding means 58 is slipped onto tip 64 of barrel 12. Once the upper conical member 62 of holding means 58 is firmly engaged with tip 64, lower portion 38 of storage container 20 is slipped off to expose hollow needle 56. Since the inoculant is already provided within barrel 12, the syringe is ready to use with a minimal amount of preparation.

It is to be understood that this is one embodiment of the invention, and modifications may be made which will still fall within the scope of the invention.

Thus, it can be seen that the invention accomplishes at least all of its objectives.

What is claimed is:

1. In a syringe having a barrel with two ends, a hollow tip at one end to receive a needle means, a plunger slidably fitting within the other end of said barrel, the improvement comprising:

a hollow center within said plunger;

a cylindrical storage compartment for holding the needle means, said compartment having a lower portion adapted to frictionally hold said needle means and an upper portion releasably connected to the lower portion for enclosing said needle means;

said storage compartment being frictionally and slidably received within said hollow center of said plunger for storing the needle means when not in use, and at least part of said upper portion extending beyond said plunger whereby said storage compartment may be grasped and removed from said plunger;

said barrel being adapted to be pre-filled with an inoculant; and a cap having cylindrical walls, an open end and a closed end, a cylindrical shoulder protruding inwardly from said closed end of said cap wherein said shoulder extends into said hollow tip and said cylindrical walls frictionally engaging said tip such that said cap seals said tip of said barrel to prevent leakage of said inoculant while said needle means is stored in said hollow center of said plunger.

2. The syringe of claim 1 wherein said cylindrical shoulder has a concave center.

3. The syringe of claim 1 wherein said cylindrical shoulder has a concave center.

4. The syringe of claim 1 wherein the needle means has fin means for frictionally engaging the lower portion of said storage compartment so as to hold said needle means within said lower portion.

* * * * *